(12) United States Patent
Odle et al.

(10) Patent No.: US 6,528,663 B1
(45) Date of Patent: Mar. 4, 2003

(54) METHODS FOR THE PREPARATION OF 4-CHLOROPHTHALIC ANHYDRIDE

(75) Inventors: Roy Ray Odle, Mt. Vernon, IN (US); Thomas Link Guggenheim, Mt. Vernon, IN (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/683,256

(22) Filed: Dec. 5, 2001

(51) Int. Cl.$^7$ ................ C07D 307/89; C07D 209/48
(52) U.S. Cl. .............. 549/246; 548/470; 548/485
(58) Field of Search ............. 549/246; 548/470, 548/485

(56) References Cited

U.S. PATENT DOCUMENTS

| | | | |
|---|---|---|---|
| 1,891,843 A | 12/1932 | Shaw et al. | |
| 2,391,226 A | 12/1945 | Clifford et al. | 260/0 |
| 2,764,597 A | 9/1956 | Barney | 260/364.3 |
| 3,240,792 A | 3/1966 | Patrick et al. | 260/346.3 |
| 3,346,597 A | 10/1967 | De Acetis | 260/346.3 |
| 3,480,667 A | 11/1969 | Siegart et al. | 260/514 |
| 3,506,689 A | 4/1970 | Peterlein | 260/346.3 |
| 3,803,085 A | 4/1974 | Takehoshi et al. | |
| 3,819,658 A | 6/1974 | Gormley et al. | 260/346.3 |
| 3,875,116 A | 4/1975 | Heath et al. | |
| 3,879,428 A | 4/1975 | Heath et al. | |
| 3,972,902 A | 8/1976 | Heath et al. | 260/346.3 |
| 3,983,093 A | 9/1976 | Williams, III et al. | |
| 4,045,408 A | 8/1977 | Griffith et al. | 260/47 |
| 4,217,281 A | 8/1980 | Markezich et al. | 260/326 A |
| 4,257,953 A | 3/1981 | Williams, III et al. | 260/326 R |
| 4,273,712 A | 6/1981 | Williams, III et al. | |
| 4,302,396 A | 11/1981 | Tsujimoto et al. | 260/346.3 |
| 4,318,857 A | 3/1982 | Webb et al. | 260/346.3 |
| 4,329,291 A | 5/1982 | Webb et al. | 549/241 |
| 4,329,292 A | 5/1982 | Webb | 549/241 |
| 4,329,496 A | 5/1982 | Webb | 562/468 |
| 4,340,545 A | 7/1982 | Webb et al. | 549/241 |
| 4,374,267 A | 2/1983 | Fifolt et al. | 562/456 |
| 4,417,044 A | 11/1983 | Parekh | 528/179 |
| 4,455,410 A | 6/1984 | Giles, Jr. | 525/436 |
| 4,514,572 A | 4/1985 | Hamprecht et al. | 549/246 |
| 4,517,372 A | 5/1985 | Tang | 549/246 |
| 4,520,204 A | 5/1985 | Evans | |
| 4,559,405 A | 12/1985 | Telschow | 549/240 |
| 4,560,772 A | 12/1985 | Telschow et al. | 549/240 |
| 4,560,773 A | 12/1985 | Telschow | 549/240 |
| 4,571,425 A | 2/1986 | Silva | 549/241 |
| 4,584,388 A | 4/1986 | Webb | 549/241 |
| 4,599,429 A | 7/1986 | Odle | 548/481 |
| 4,612,361 A | 9/1986 | Peters | |
| 4,675,376 A | 6/1987 | Peters | |
| 4,680,412 A | 7/1987 | Hamprecht et al. | 548/480 |
| 4,902,809 A | 2/1990 | Groeneweg et al. | 548/481 |
| 4,921,970 A | 5/1990 | Odle | 548/480 |
| 4,962,206 A | 10/1990 | Cocoman et al. | 549/246 |
| 4,965,337 A | 10/1990 | Peters et al. | |
| 4,978,760 A | 12/1990 | Spohn | 549/246 |
| 5,003,088 A | 3/1991 | Spohn et al. | 549/246 |
| 5,021,588 A | 6/1991 | Contractor | 549/259 |
| 5,049,682 A | 9/1991 | Tang et al. | 549/246 |
| 5,059,697 A | 10/1991 | Fertel et al. | 549/246 |
| 5,132,423 A | 7/1992 | Brunelle et al. | 544/162 |
| 5,155,234 A | 10/1992 | Odle | 549/243 |
| 5,206,391 A | 4/1993 | Seper et al. | 549/246 |
| 5,229,482 A | 7/1993 | Brunelle | 528/125 |
| 5,233,054 A | 8/1993 | Tang et al. | 549/246 |
| 5,235,071 A | 8/1993 | Ueda et al. | 549/248 |
| 5,266,678 A | 11/1993 | Perry et al. | 528/322 |
| 5,300,201 A | 4/1994 | Seper et al. | 204/157.6 |

(List continued on next page.)

FOREIGN PATENT DOCUMENTS

JP          10237063         * 9/1998

*Primary Examiner*—Ceila Chang
*Assistant Examiner*—Golam M. M. Shameem

(57) ABSTRACT

A method for the synthesis of substituted phthalic anhydrides (IV)

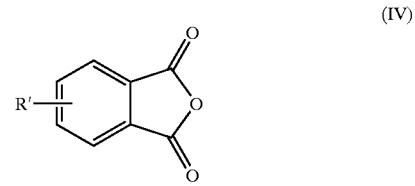

(IV)

wherein R' is a halogen, aromatic or aliphatic group comprising 1–18 carbons, hydrogen or nitro group is the transimidation between a substituted N-alkyl phthalimide (V)

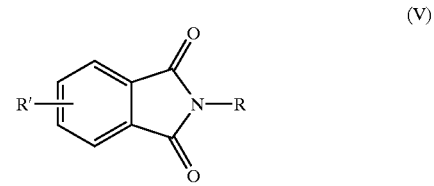

(V)

wherein R is an alkyl having from 1 to 18 carbons, and a substituted tetrahydrophthalic anhydride (VI):

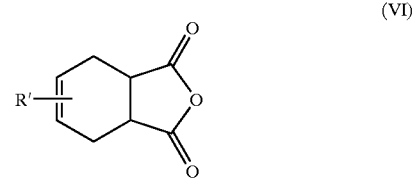

(VI)

The by-product of this reaction, a substituted N-alkyl tetrahydrophthalimide (VII), may be converted by aromatization to the substituted N-alkyl phthalimide (V).

5 Claims, No Drawings

U.S. PATENT DOCUMENTS

| | | |
|---|---|---|
| 5,322,954 A | 6/1994 | Seper et al. ............... 549/246 |
| 5,359,084 A | 10/1994 | Dellacoletta et al. |
| 5,359,092 A | 10/1994 | Hay et al. .................... 546/99 |
| 5,364,824 A | 11/1994 | Andrews et al. ........... 502/209 |
| 5,459,227 A | 10/1995 | Hay et al. ................... 528/211 |
| 5,510,308 A | 4/1996 | Kourtakis .................. 502/209 |
| 5,536,846 A | 7/1996 | Dellacoletta et al. |
| 5,557,005 A | 9/1996 | Semler et al. ................ 560/47 |
| 5,672,750 A | 9/1997 | Perry ......................... 564/132 |
| 5,683,553 A | 11/1997 | Baur et al. ..................... 203/1 |
| 5,705,685 A | 1/1998 | Lyons et al. ............... 562/549 |
| 5,719,295 A | 2/1998 | Dellacoletta et al. |
| 5,750,777 A | 5/1998 | Aubry et al. ............... 562/549 |
| 5,779,792 A | 7/1998 | Atami et al. ................ 117/214 |
| 5,792,719 A | 8/1998 | Eberle et al. ............... 502/178 |
| 5,872,294 A | 2/1999 | Caringi et al. .............. 564/240 |
| 5,908,915 A | 6/1999 | Brunelle |
| 5,936,099 A | 8/1999 | Dellacoletta et al. |
| 6,008,374 A | 12/1999 | Dellacoletta et al. |
| 6,011,122 A | 1/2000 | Puyenbroek |
| 6,072,010 A | 6/2000 | Puyenbroek |
| 6,235,866 B1 | 5/2001 | Khouri et al. |
| 6,265,521 B1 | 7/2001 | Fyvie et al. |

* cited by examiner

METHODS FOR THE PREPARATION OF 4-CHLOROPHTHALIC ANHYDRIDE

CROSS REFERENCE TO RELATED APPLICATIONS

Not Applicable

FEDERAL RESEARCH STATEMENT

Not Applicable

BACKGROUND OF INVENTION

This invention relates to a preparation of anhydrides. More particularly, it relates to a transimidation-based method for the preparation of anhydrides.

Polyetherimides are high heat engineering plastics having a variety of uses. As disclosed in U.S. Pat. No. 5,229,482, one route for the synthesis of polyetherimides proceeds through a bis(4-chlorophthalimide) having the following structure (I)

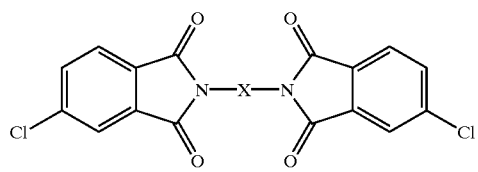

(I)

wherein X is a divalent, alkylene, cycloalkylene, or arylene moiety. The bis(4-chlorophthalimide) wherein X is a 1,3-phenyl group (II) is particularly useful.

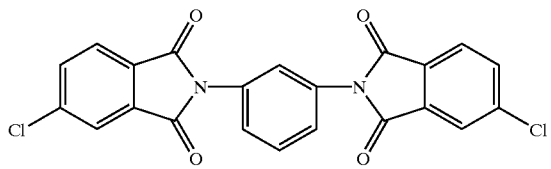

(II)

Bis(chlorophthalimide)s (I) and (II) are typically formed by the condensation of amines, e.g., 1,3-diaminobenzene with anhydrides, e.g., 4-chlorophthalic anhydride (III)

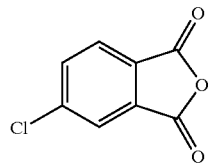

(III)

4-Chlorophthalic anhydride is an expensive starting material which presently must be custom synthesized. Current routes for the synthesis of 4-chlorophthalic anhydride lead to mixtures of isomers, which are difficult to separate, or are prohibitively costly. For example, the Diels-Alder condensation of maleic anhydride with 2-chloro-1,3-butadiene to yield 4-chlorotetrahydrophthalic anhydride, followed by aromatization in the presence bromine requires the subsequent recovery of HBr. Attempted thermal aromatization of 4-chloro-tetrahydrophthalic anhydride results in low yields of 4-chlorophthalic anhydride and tar formation. This and other routes are described in U.S. Pat. Nos. 5,059,697; 5,003,088; 5,322,954; 4,978,760 and 5,233,054.

SUMMARY OF INVENTION

A new method for the synthesis of phthalic anhydrides (IV)

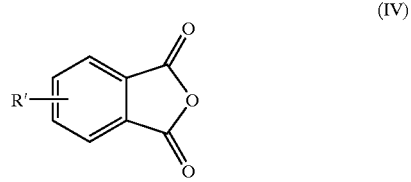

(IV)

wherein R' is a halogen, an aromatic or aliphatic group comprising 1 to about 18 carbons, a hydrogen or a nitro group is the transimidation between the corresponding N-alkyl phthalimide (V)

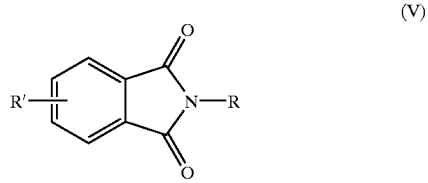

(V)

wherein R' in (IV) and R' in (V) are identical, and further wherein R is an alkyl group having from 1 to about 18 carbons, and a tetrahydrophthalic an hydride (VI)

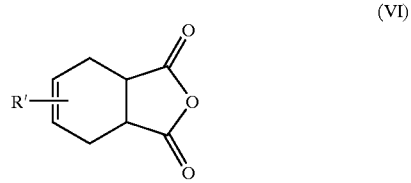

(VI)

The by-product of the transimidation is an N-alkyl tetrahydrophthalimide (VII)

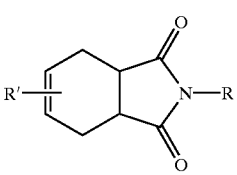

(VII)

In an advantageous feature of this method, where R' in (V), (VI) and (VII) are identical, N-alkyl tetrahydrophthalimide (VII) may be converted by aromatization to produce the corresponding N-alkyl phthalimide (V).

DETAILED DESCRIPTION

A convenient route for the formation of phthalic anhydrides (IV) is via transimidation between the corresponding N-alkyl phthalimide (V) and a tetrahydrophthalic anhydride (VI). A by-product of this reaction is an N-alkyl tetrahydrophthalimide (VII). This by-product is preferably converted to yield the corresponding N-alkyl phthalimide (V).

The product phthalic anhydrides (IV) have the structure

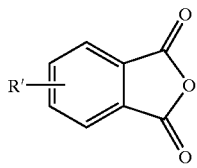

(IV)

wherein R' is a halogen, an aromatic or aliphatic group comprising 1 to about 18 carbons, a hydrogen or a nitro group.

The starting N-alkyl phthalimides (V) have the structure

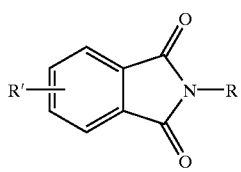

(V)

wherein R' is as described above, and R is a straight chain or branched alkyl group having from 1 to about 18 carbons, for example methyl, ethyl, propyl, and the like. N-alkyl phthalimides (V) may be obtained from the corresponding N-alkyl tetrahydrophthalimide by aromatization. Aromatization may be achieved by any method known in the art, such as those taught by U.S. Pat. Nos. 5,233,054; 5,003,088; 5,059,697 and 4,978,760. Aromatization may also be achieved by passing the N-alkyl tetrahydrophthalimide over a transition metal catalyst such as $V_2O_5$ at a temperature in the range of about 250° C. to about 270° C. Alternately, N-alkyl phthalimides (V) may be obtained by heating a tetrahydrophthalic anhydride with the desired alkyl amine or aryl amine at a temperature of about 50° C. to about 250° C. for up to about 5 hours. The resulting product, N-alkyl phthalimide may be isolated by any method known in the art such as distillation or column chromatography.

Tetrahydrophthalic anhydrides (VI)

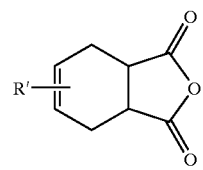

(VI)

wherein R' is as defined above may be obtained by the Diels-Alder condensation of dienophile maleic anhydride with a diene substituted by R'. Conditions for this reaction are known in the chemical literature. Suitable R' substitutions include, but are not limited to, halogen, aromatic or aliphatic groups comprising 1 to about 18 carbons, hydrogen or nitro group. A preferred diene is 2-chloro-1,3-butadiene (chloroprene).

An advantageous feature of this method is that where R' are identical in both (V) and (VI), the by-product of the transimidation, N-alkyl tetrahydrophthalimide (VII)

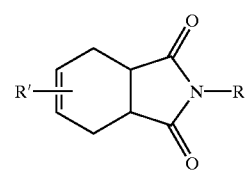

(VII)

can be converted by aromatization to produce N-alkyl phthalimide (V) as discussed above. Due to this advantageous feature it is contemplated that the synthesis of 4-chlorophthalic anhydrides may be practiced in a batchwise or continuous fashion.

As shown in Scheme I this method is particularly suitable for the formation of 4-chlorophthalic anhydride (III), which is an important intermediate in the synthesis of polyetherimides.

Scheme I

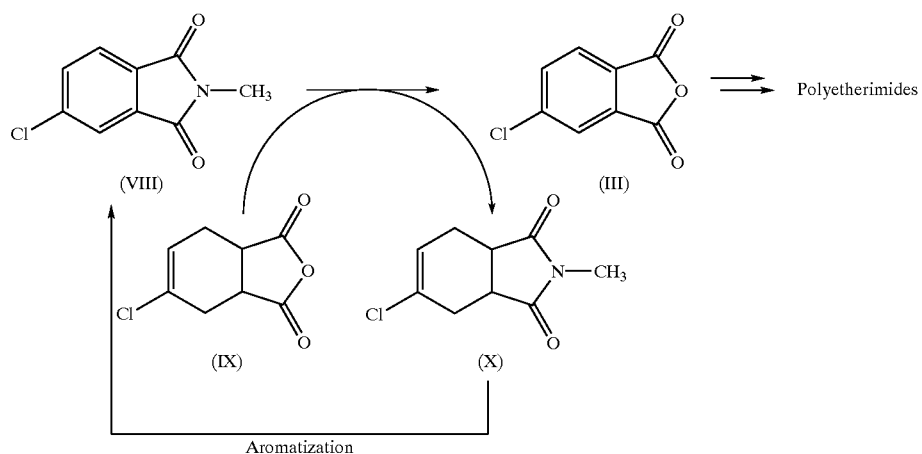

Aromatization

Accordingly, 4-chlorophthalic anhydride (III) is produced by transimidation of N-methyl-4-chlorophthalimide (VIII) with 4-chlorotetrahydrophthalic anhydride (IX). The by-product of the transimidation, N-methyl-4-chlorotetrahydrophthalimide (X) is preferably converted by aromatization to N-methyl-4-chlorophthalimide (VIII).

All patents cited herein are incorporated by reference.

The invention is further described by the following non-limiting examples:

EXAMPLES

Example 1

Synthesis of N-methyl-4-chlorophthalimide (VIII).

An appropriately equipped glass reaction vessel was charged with 186.5 grams (1 mole) of 4-chlorotetrahydrophthalic anhydride and heated to 150° C. under nitrogen. Methylamine gas (32 grams, 1.03 mole) was then introduced to the reaction vessel subsurface over 30 minutes. The reaction mixture was then heated for 3 hours at 180° C. The product was then distilled to give N-methyl-4-chlorophthalimide in approximately 95% yield.

Example 2

Synthesis of 4-Chlorotetrahydrophthalic Anhydride (IX).

156.9 g (1.6 mole) of maleic anhydride and 250 ml toluene were added to a flask. 25 ml of toluene was removed by distillation to dry the solution. 150 g (1.69 mole) of chloroprene dissolved in 250 ml of xylene was slowly added to the flask. The entire addition took 30 minutes. The resulting solution was then heated at 55° C. for three hours. The solution was then distilled to remove solvents. The remaining material was distilled at 160–165° C. (1 to 2 mm pressure) to afford 4-chlorotetrahydrophthalic anhydride in 85% yield (253 grams).

Example 3

Synthesis of 4-Chlorophthalic Anhydride (III)

A resealable 50-ml stainless steel tube was charged with 1.5 g 4-chlorotetrahydrophthalic anhydride, 0.262 g N-methyl-4-chlorophthalimide, 0.841 g triethylamine, and 20 ml of water. The tube was sealed and heated in an oil bath at 170° C. for 3 hours, and then cooled to room temperature.

A small sample of the aqueous phase was analyzed by GCMS. The analysis showed that 83.2% exchange had occurred. Analysis further showed that the reaction mixture was composed of 2.4 mol % of N-methyl-4-chlorophthalimide, 11.9 mol % of N-methyl-4-chloro tetrahydrophthalimide, 11.9 mol % of 4-chlorophthalic anhydride (as the triethylamine salt of the corresponding diacid), and 73.8 mol % of 4-chlorotetrahydrophthalic anhydride (as the triethylamine salt of the corresponding diacid).

The aqueous phase was extracted with 20 ml of toluene containing 3 wt % triethylamine in a separatory funnel at room temperature. The toluene extraction effectively removed the N-methyl-4-chlorotetrahydrophthalimide and the unreacted N-methyl-4-chlorophthalimide from the aqueous phase. The aqueous phase still contained the 4-chlorophthalic anhydride (as the triethylamine salt of the corresponding diacid), and the 4-chlorotetrahydrophthalic anhydride (as the triethylamine salt of the corresponding diacid). The aqueous phase was distilled, during which the triethylamine salts cracked to liberate water and triethylamine, with the formation of 4-chlorophthalic anhydride and 4-chlorotetrahydrophthalic anhydride. The water and triethylamine were taken overhead, and the still bottoms were collected. The still bottoms were then distilled to separate the 4-chlorotetrahydrophthalic anhydride from the 4-chlorophthalic anhydride. The 4-chlorotetrahydrophthalic anhydride was recombined with the water and TEA previously collected, and reused.

Example 4

Conversion of N-methyl-4-chlorotetrahydrophthalimide (X) to N-methyl-4-chlorophthalimide.

Gas phase reactions were carried out in a hot-tube reactor that was packed with about 13 grams of a catalyst containing $V_2O_5$. The inlet of the hot-tube reactor was connected to a flow controller and heated syringe pump. The flow controller managed the flow of purified air. The heated syringe pump contained 4-chloro-N-methyl tetrahydrophthalimide and delivered it to the hot tube reactor at a constant rate of 0.05 milliliters per minute. The outlet of the hot tube reactor was connected to a receiver cooled in an ice-bath where the reaction products were collected. The hot-tube reactor was maintained at the 260° C. The reaction product was analyzed by gas chromatographic techniques after the system had equilibrated for 10–20 minutes. At a flow rate of 90 ml/min all of the N-methyl-4-chlorotetrahydrophthalimide was converted to N-methyl-4-chlorophthalimide.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for preparing a phthalic anhydride, comprising: transimidation of an N-alkyl phthalimide (V)

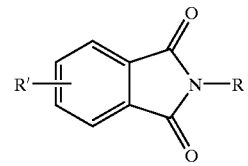

(V)

wherein R' is selected from the group consisting of halogens, aromatic groups comprising 6–18 carbons, aliphatic groups comprising 1–18 carbons, hydrogen and nitro groups, and R is an alkyl group having from 1 to 18 carbons, with substituted tetrahydrophthalic anhydride (VI)

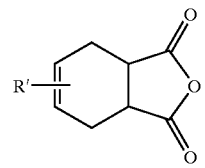

(VI)

wherein R" is selected from the group consisting of halogen, aromatic groups comprising 6–18 carbons, or aliphatic group comprising 1–18 carbons, hydrogen and nitro groups, to yield a substituted N-alkyl tetrahydrophthalimide (VII)

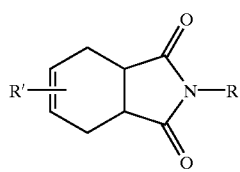

and a phthalic anhydride (IV)

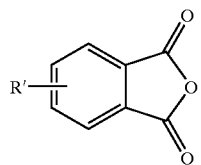

2. The method of claim 1, wherein the phthalic anhydride is 4-chlorophthalic anhydride and the N-alkyl phthalimide is a N-alkyl-4-chlorophthalimide.

3. The method of claim 1, further comprising converting the N-alkyl tetrahydrophthalimide by aromatization to the corresponding N-alkyl phthalimide.

4. The method of claim 3, wherein the N-alkyl tetrahydrophthalimide is converted to the corresponding N-alkyl phthalimide in the presence of vanadium oxide.

5. The method of claim 1, wherein the N-alkyl tetrahydrophthalimide (VII) is N-methyl-4-chlorotetrahydrophthalimide.

* * * * *

UNITED STATES PATENT AND TRADEMARK OFFICE
CERTIFICATE OF CORRECTION

PATENT NO. : 6,528,663 B1
DATED : March 4, 2003
INVENTOR(S) : Odle et al.

It is certified that error appears in the above-identified patent and that said Letters Patent is hereby corrected as shown below:

Title page,
Item [73], Assignee, delete "Pittsfield, MA" and insert -- Schenectady, NY --.

Column 1,
Line 64, between "presence" and "bramine" insert -- of --.

Column 2,
Line 33, delete "an hydride" and insert -- anhydride --.

Column 4,
Line 14, delete "is".
Line 23, delete "are" and insert -- is --.

Signed and Sealed this

Third Day of January, 2006

JON W. DUDAS
*Director of the United States Patent and Trademark Office*